United States Patent
Lapitsky et al.

(10) Patent No.: US 10,010,078 B2
(45) Date of Patent: *Jul. 3, 2018

(54) ANTIBACTERIAL SURFACTANT/MICROGEL FORMULATIONS, METHODS OF MAKING AND METHODS OF USING THE SAME

(71) Applicant: The University of Toledo, Toledo, OH (US)

(72) Inventors: Yakov Lapitsky, Toledo, OH (US); Youngwoo Seo, Toledo, OH (US); Kristopher Richardson, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/382,968

(22) Filed: Dec. 19, 2016

(65) Prior Publication Data
US 2017/0099838 A1  Apr. 13, 2017

Related U.S. Application Data

(63) Continuation of application No. 14/406,618, filed as application No. PCT/US2013/044753 on Jun. 7, 2013, now Pat. No. 9,560,849.

(60) Provisional application No. 61/657,787, filed on Jun. 9, 2012.

(51) Int. Cl.
| | |
|---|---|
| A01N 25/00 | (2006.01) |
| A01N 43/00 | (2006.01) |
| A01N 43/16 | (2006.01) |
| A01N 25/30 | (2006.01) |
| A01N 25/22 | (2006.01) |
| C08B 37/08 | (2006.01) |
| A01N 25/04 | (2006.01) |
| A01N 31/14 | (2006.01) |
| A01N 41/02 | (2006.01) |

(52) U.S. Cl.
CPC ............ *A01N 43/16* (2013.01); *A01N 25/04* (2013.01); *A01N 25/22* (2013.01); *A01N 25/30* (2013.01); *A01N 31/14* (2013.01); *A01N 41/02* (2013.01); *C08B 37/003* (2013.01)

(58) Field of Classification Search
CPC ........ A01N 25/30; A01N 43/16; A01N 25/04; A01N 25/22; A01N 31/14; A01N 41/02; A01N 37/003
See application file for complete search history.

(56) References Cited

U.S. PATENT DOCUMENTS

| | | | | |
|---|---|---|---|---|
| 4,822,598 A | * | 4/1989 | Lang | A61K 8/736 424/47 |
| 6,306,835 B1 | * | 10/2001 | Daly | A01N 43/16 424/400 |
| 6,649,192 B2 | * | 11/2003 | Alonso Fernandez | A61K 9/5161 424/499 |
| 2009/0117195 A1 | * | 5/2009 | Kauper | A61K 8/0241 424/493 |

FOREIGN PATENT DOCUMENTS

WO   WO 2011082840 A1 *  7/2011  ............... C11D 1/83

OTHER PUBLICATIONS

Lim. Synthesis of a Fiber-Reactive Chitosan Derivative and Its Application to Cotton Fabric as an Antimicrobial Finish and a Dyeing-Improving Agent. PhD Thesies. 2002, North Carolina State University.*

* cited by examiner

*Primary Examiner* — Robert A Wax
*Assistant Examiner* — Olga V Tcherkasskaya
(74) *Attorney, Agent, or Firm* — MacMillan, Sobanski & Todd, LLC

(57) ABSTRACT

Formulations having, as active agents, at least one quaternized polymeric microgel and at least one nonionic surfactant, methods of making, and methods of using are described.

20 Claims, 8 Drawing Sheets
(8 of 8 Drawing Sheet(s) Filed in Color)

| SDS:TX-100 Molar Ratio | [SDS] at Precipitation Point (mmol/kg) | [SDS] + [TX-100] at Precipitation Point (mmol/kg) |
|---|---|---|
| 100:0 | 1.89 ± 0.14 | 1.89 ± 0.14 |
| 70:30 | 0.95 ± 0.17 | 1.37 ± 0.25 |
| 40:60 | 0.60 ± 0.18 | 1.50 ± 0.46 |
| 10:90 | 0.16 ± 0.05 | 1.60 ± 0.52 |

ANTIBACTERIAL SURFACTANT/MICROGEL FORMULATIONS, METHODS OF MAKING AND METHODS OF USING THE SAME

CROSS REFERENCE TO RELATED APPLICATIONS

This is a continuation application of U.S. application Ser. No. 14/406,618, filed under 35 U.S.C. § 371 on Dec. 9, 2014, now allowed; which is the national stage entry of international application PCT/US2013/044753, filed under the authority of the Patent Cooperation Treaty on Jun. 7, 2013, published; which claims the benefit of U.S. Patent Application No. 61/657,787 filed Jun. 9, 2012. The entire disclosures of all the aforementioned applications are expressly incorporated herein by reference for all purposes.

STATEMENT REGARDING FEDERALLY SPONSORED RESEARCH

This invention was made with U.S. government support under Grant No. CBET-1133795 awarded by the National Science Foundation. The United States Government has certain rights in the invention.

BACKGROUND OF THE INVENTION

Antibacterial surfactant formulations are often prepared using toxic antibacterial agents (e.g., cationic surfactants, alkyltrimethylammonium salts). Consequently, their use in cleaning formulations raises environmental concerns.

SUMMARY OF THE INVENTION

In a first broad aspect, described herein is an antimicrobial formulation comprised of: at least one nonionic surfactant capable of providing colloidal stability to the formulation, and at least one quaternized polymeric microgel capable of being dispersed in the nonionic surfactant. The quaternized polymeric microgel is comprised of one or more of: chitosan oligomers or chitosan polymers. Further, the antimicrobial formulation is essentially free of cationic surfactants.

In certain embodiments, the chitosan oligomer or chitosan polymer comprises one or more of: chitin, a chitin derivative, chitosan, chitosan derivatives, and cross-linked quaternized chitosans or derivatives thereof.

In certain embodiments, the formulation consists essentially of the nonionic surfactant and the quaternized polymeric microgel, wherein the concentration of the quaternized polymeric microgel ranges from about 0.01 wt. % to about 0.5 wt. %., per volume in water.

In certain embodiments, the formulation consists essentially of the nonionic surfactant and the quaternized polymeric microgel, wherein the concentration of the quaternized polymeric microgel is about 0.1 wt. %, per volume in water.

In certain embodiments, the nonionic surfactant is present at a concentration, based on the weight of the formulation, of: about 250 mmol/kg or less; about 100 mmol/kg or less; about 25 mmol/kg or less; about 15 mmol/kg or less; or, about 5 mmol/kg or less.

In certain embodiments, the nonionic surfactant comprises one or more of: polyoxypropylene glycol alkyl ethers, and glycol octylphenol ethers. In certain embodiments, the nonionic surfactant comprises one or more of: ethoxylated alkylphenols, glucoside alkyl ethers, and polyoxyethylene glycol alkylphenol ethers. In certain embodiments, the ethoxylated alkyphenols comprise ethoxylated octylphenol.

In certain embodiments, the nonionic surfactant comprises t-octylphenoxypolyethoxyethanol (TX-100), and wherein the quaternized polymeric microgel comprises N-[(2-hydroxy-3-trimethylammonium) propyl] chitosan chloride (HTCC).

In certain embodiments, the formulation comprises: t-octylphenoxypolyethoxyethanol (TX-100) at a concentration ranging from about 0.05% to about 1%, by weight, per volume in water; and, N-[(2-hydroxy-3-trimethylammonium) propyl] chitosan chloride (HTCC) at a concentration ranging from about 0.3% to about 3%, by weight, per volume in water.

In certain embodiments, the quaternized polymeric microgel is prepared through ionic cross-linking of quaternized chitosan with sodium tripolyphosphate (TPP).

In certain embodiments, the quaternized polymeric microgel comprises particles having a size distribution of about 10 nm to about 1000 nm; about 200 nm to about 400 nm; or, about 10 nm to about 100 nm.

In certain embodiments, the antimicrobial formulation comprises: at least one nonionic surfactant present at a total concentration in the antimicrobial formulation in the range of from about 0.05% to about 3%, by weight, per volume in water; and, one or more microgels comprising quaternized polymeric microgel comprised of one or more of: chitosan oligomers or chitosan polymers; the total concentration of the quaternized polymeric microgels in the antimicrobial formulation ranging from about 0.01% to about 0.15%, by weight, per volume in water.

In certain embodiments, the nonionic surfactant is present in admixture with at least one anionic surfactant, wherein the anionic surfactant is present at a concentration wherein amine groups on the quaternized polymeric microgel are not neutralized.

In certain embodiments, the anionic:nonionic ratio is about 30:70. In certain other embodiments, the anionic:nonionic ratio is about 40:60. Also, in certain embodiments, the anionic surfactant is present at a concentration, based on the weight of the formulation of: about 2 mmol/kg or less; about 1 mmol/kg or less; or, about 0.5 mmol/kg or less.

In certain embodiments, the surfactant admixture comprises about 40:60 anionic:nonionic surfactant, and wherein the microgel is dispersed in about 3 mmol/kg or less, based on the weight of the formulation, of the surfactant admixture.

In certain embodiments, the anionic surfactant comprises one or more alkali metal $C_{8-18}$ alkyl sulfates. In certain embodiments, wherein the alkali metal $C_{8-18}$ alkyl sulfates are selected from the group consisting of: sodium lauryl sulphate, sodium laureth sulfates, alkyl ether sulfates, alkyl benzene sulfonates, fatty acids, and fatty acid salts.

In another aspect, described herein are uses of the formulation where such formulation is in the form of a tablet, powder, gel, capsule, liquid, coating, film, foam, sponge, woven material, non-woven material, textile material, knitted material, porous material or solid material.

In another aspect, described herein are articles comprising a porous or solid material at least partially coated with the formulation; and/or at least partially comprised of the formulation.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the Patent Office upon request and payment of the necessary fee.

DETAILED DESCRIPTION OF THE INVENTION

Figure 1:
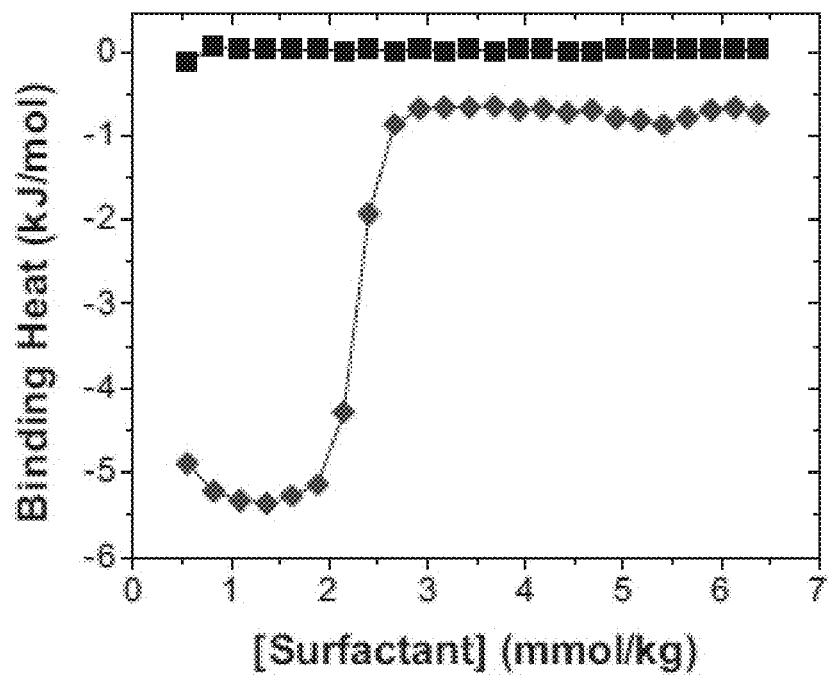
FIG. 1: Isothermal titration calorimetry (ITC) data for (♦) sodium dodecyl sulfate (SDS) and (■) t-octylphenoxy polyethoxyethanol (TX-100) binding to chitosan-based microgels. (The lines are guides.)

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The use of the word "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In any embodiment discussed in the context of a numerical value used in conjunction with the term "about," it is specifically contemplated that the term "about" can be omitted.

The terms "a" and "an," when used in conjunction with the word "comprising" in the claims or specification, denotes one or more, unless specifically noted.

All percentages, parts and ratios are based upon the total weight of the compositions of the present invention, unless otherwise specified. All such weights as they pertain to listed ingredients are based on the active level and, therefore, may not include solvents or by-products that may be included in commercially available materials, unless otherwise specified. The term "weight percent" may be denoted as "wt. %" herein. All molecular weights as used herein are weight average molecular weights, unless otherwise specified.

The terms "nil-cationic surfactant" or "substantially or essentially free of a cationic surfactant," as used herein, means that the formulations comprise very low levels of cationic surfactant, and preferably no cationic surfactant. For example, "essentially free" can means less than 1% by weight, preferably less than 0.5% by weight, more preferably less than 0.1% by weight, and even more preferably less than 0.01% by weight of a component based on the total weight of the composition.

The term "antimicrobial" generally refers to the microbicidal or microbistatic properties of a formulation that enables such to kill, destroy, inactivate or neutralize a microorganism; or to prevent or reduce the growth, ability to survive, or propagation of a microorganism.

The term "zeta-potential" or "ζ-potential" generally refers to the electrical potential that exists across the interface of all solids and liquids, e.g., the potential across the diffuse layer of ions surrounding a charged colloidal particle. Zeta potential can be calculated from electrophoretic mobilities, i.e., the rates at which colloidal particles travel between charged electrodes placed in contact with the substance to be measured, using techniques well known in the art.

The term "surfactant" as used herein includes dispersing agents, suspending agents, emulsion stabilizers and detergents.

Nonionic Surfactants

In particular embodiments, "surfactant" includes nonionic surfactants. Non-limiting examples of nonionic surfactants include: polyoxypropylene glycol alkyl ethers, and glycol octylphenol ethers; ethoxylated alkylphenols, glucoside alkyl ethers, and polyoxyethylene glycol alkylphenol ethers, such as ethoxylated octylphenol.

In one embodiment, the nonionic surfactant comprises t-octylphenoxypolyethoxyethanol (other names 4-(1,1,3,3-tetramethylbutyl)phenyl-polyethylene glycol, t-octylphenoxypolyethoxyethanol, polyethylene glycol tert-octylphenyl ether) $(C_{14}H_{22}O(C_2H_4O)_n)$ (also known as Triton X-100 or TC-100) is a nonionic surfactant that has a hydrophilic polyethylene oxide chain (on average it has 9.5 ethylene oxide units) and an aromatic hydrocarbon lipophilic or hydrophobic group. The hydrocarbon group is a 4-(1,1,3,3-tetramethylbutyl)-phenyl group.

In certain embodiments, the formulations comprise up to about 250 mmol/kg of nonionic surfactant. In particular embodiments, the formulations comprise a nonionic surfactant present at a concentration of about 100 mmol/kg, or about 25 mmol/kg, or about 15 mmol/kg, or about 5 mmol/kg.

In certain embodiments, the formulations comprise nonionic surfactant in concentrations ranging from about 0.05% w/v in water to about 3% w/v in water.

In certain other embodiments, the formulations comprise nonionic surfactant in concentrations ranging from about 0.05% w/v in water to about 50% w/v in water.

Microgels

The term "quaternized polymers" generally refers to the building blocks for the microgels. In certain embodiments, the quaternized polymers comprise quaternized cellulose derivatives. In certain other embodiments, the quaternized polymers comprise chitosan and derivatives thereof. In certain other embodiments, bio-polymers other than chitosan are also possible, such as agarose and dextran.

The term "microgels" includes the quaternized polymers, as described herein. Also, in certain embodiments, the microgels can be comprised of synthetic polymers with quaternary amine sidechain groups. In still other embodiments, the microgels can be prepared though the covalent or ionic cross-linking of synthetic polymers with cationic monomer units, or through polymerization of multifunctional monomers. For example, while not wishing to be bound by theory, it is believed that chitosan has antibacterial activity due to the amine groups on its glucosamine monomer units, and is further strengthened through the substitution of the glucosamine primary amines with quaternary amines. In addition to enhancing the antibacterial activity, this "quaternization" of chitosan also enhances its solubility at neutral and alkaline pH.

In a particular embodiment, chitosan (or its quaternized derivatives, e.g., trimethylchitosan, or quaternized chitosan) is prepared as cross-linked particles (i.e., micro- or nanogels) which increases the antibacterial activity greater than that of the chitosan derivatives in the molecular form.

The term "chitosan" as used herein generally includes a cationic polyelectrolyte derived from the naturally abundant biopolymer, chitin. In certain embodiments, chitosan is composed of cationic D-glucosamine and nonionic N-acetyl-D-glucosamine monomer units, and is soluble in acidic aqueous solutions (at pH<6), where the pH-sensitive primary amine groups on the glucosamine monomer units become charged. This switchable amine group enables chitosan to form a variety of gel-like structures through its exposure to alkaline solutions, or its complexation with oppositely-charged counterions, polymers and surfactants.

Suitable chitosan derivatives include, but are not limited to: N-[(2-hydroxy-3-trimethylammonium) propyl] chitosan chloride (HTCC); hydroxyalkyl chitosans, such as hydroxypropyl chitosan; N,N,N-trimethyl chitosan (TMC); N-propyl-(QuatPropyl), N-butyl-(QuatButyl) and N-hexyl (QuatHexyl)-N,N-dimethyl chitosan; N-(4-N,N-dimethylaminocinnamyl) chitosan chloride; N,N-octylchitosan; N-benzylchitosan; N-(4-methylbenzylchitosan); N-(4-hydroxybenzyl) chitosan; N-(2-methoxybenzyl) chitosan; N-(4-methoxybenzyl) chitosan; N-(3,4-dimethoxybenzyl) chitosan; N-(4-fluorobenzyl) chitosan; N-(4-chlorobenzyl) chitosan; N-(3-bromobenzyl) chitosan; N-(4-bromobenzyl) chitosan; N-(4-trifluorobenzyl) chitosan; N-(4-nitrobenzyl) chitosan; N-(4-carboxybenzyl) chitosan; N-(4-pyridinylmethyl) chitosan; N-(2-thiophenylmethyl) chitosan, and combinations thereof.

In certain embodiments, the quaternized polymeric microgel comprises a saccharide. In certain embodiments, the quaternized polymeric microgel comprises a biodegradable linear polysaccharide having glucosamine units. In certain embodiments, the quaternized polymeric microgel is selected from chitosan, chitosan derivatives, cellulose, chitin, chitin derivatives, and combinations thereof.

The quaternized chitosan microgels are useful in the preparation of antibacterial surfactant formulations for use in cleaning and personal care products. For example, dilute chitosan-based microgel formulations are useful as replacements or substitutes for cationic surfactants and other toxic small molecule antibacterial agents (e.g., triclosan or bleach) in personal care and/or cleaning products. The quaternized chitosan microgels are antibacterial even at very low concentrations and are cytocompatible with mammalian cells. In the formulations described herein, the antibacterial cationic microgels are dispersed in non-toxic nonionic surfactant solutions. In certain embodiments, these formulations achieve desirable antibacterial activity without the use of cationic surfactants or other small molecule antibacterial agents, which cationic surfactants are often toxic.

The formulations further comprise a quaternized polymeric microgel at a concentration ranging from about 0.01% by weight to about 0.5% by weight, or more preferably from about 0.1% by weight to about 0.3% by weight.

In certain embodiments, the formulations comprise a quaternized polymeric microgel at concentrations ranging from about 0.01% w/v in water to about 0.15% w/v in water.

In other certain embodiments, the formulations comprise a quaternized polymeric microgel at concentrations ranging from about 0.01% w/v in water to about 20% w/v in water, and in other embodiments, to about 50%. It is to be understood, that in certain embodiments, the volume may range from about, at least about, or at most about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, and up to about 20%, or up to about 50%. or any range derivable therein.

In certain embodiments, the quaternized polymeric microgel has a zeta-potential of about 15 mV or less. In certain embodiments, the quaternized polymeric microgel has a size distribution of about 10 nm to about 1000 nm, or from about 200 nm to about 400 nm, or from about 10 nm to about 100 nm.

Antimicrobial Formulations

Also described herein are formulations having quaternized chitosan microgels where the active agents (comprising the microgels and a nonionic surfactant) are present at concentrations effective to reduce bacterial counts.

The surfactant solubilizes hydrophobic compounds (e.g., oil in emulsions or different types of soils on clothing), while the microgels provide strong antibacterial activity without the use of cationic surfactants or other types of toxic small molecule antibacterial agents (such as triclosan or bleach). The nonionic surfactant (1) does not undermine the antibacterial activity of the microgels; and (2) does not cause the microgels to precipitate out of the mixture.

In certain embodiments, the formulations exhibit high antimicrobial activity, thus allowing for the use of low concentrations of the active agents to obtain rapid killing of large numbers of microbes upon contact. Accordingly, the low concentration formulations disclosed herein have surprising activity in reducing microbial populations on the surface of an article without impacting the properties of the article's surface.

Concentrates

Any of the formulations described herein can be prepared as concentrates. By way of non-limiting example, the formulations could be prepared with concentrations of nonionic surfactant up to about 2,500 mmol/kg, and with quaternized polymeric microgels at concentrations up to about 10% by weight. The concentrates could then be diluted down to the desired concentrations of active agents prior to use. There are many other methods of preparing the formulations described herein that will be readily apparent to the skilled practitioner.

Surfactants comprised of Anionic/Nonionic Admixtures

In certain embodiments, the nonionic surfactant is present in admixture with at least one anionic surfactant. The ratio of anionic:nonionic surfactant can be about 0:100. In particular embodiments, the anionic:nonionic surfactant ratio is 10:90, 20:80, 30:70, or 40:60. In certain embodiments, the concentration of the anionic surfactant is 2 mmol/kg or less, 1 mmol/kg or less, or 0.5 mmol/kg or less. Non-limiting examples of anionic surfactants include, for example, sodium dodecyl sulfate (SDS), sodium laureth sulfate (SLS), disulfosuccinate (DSS), alkyl benzene sulphonates, sulphated fatty alcohols, fatty acids and fatty acid salts, and the like.

Methods

Further described herein are methods of formulating chitosan-based microgel formulations with surfactants. Such methods overcome the issues that arise due to the electrostatic binding between oppositely charged surfactants and polymers. In addition, this binding can lead to the precipitation of the surfactant/polymer complex, thereby complicating the formulation of single-phase surfactant/microgel formulations. Furthermore, by binding to the chitosan, the surfactant may reduce the availability of the cationic amine groups that underlie the biocidal activity of the microgels (which could inactivate their antibacterial properties).

Also described herein are antibacterial surfactant/microgel formulations that use one or more of anionic, nonionic, and anionic/nonionic surfactant systems. The binding of anionic and nonionic surfactants to the microgels was probed by electrophoretic light scattering and isothermal titration calorimetry (ITC). The surfactant/chitosan-based microgel formulations were determined to have desirable: (1) colloidal stability, which is essential for maintaining the formulation in a single phase; (2) antibacterial activity, which is necessary to inactivate bacteria using minimal chitosan quantities; (3) hydrophobe solubilization properties, which reflect the ability to remove soils or deliver essential oils; and (4) the effect of surfactants on dispersion clarity, which is often desirable for designing aesthetically-appealing products.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

EXAMPLES

Materials and Methods
Materials

All experiments were performed using Millipore Direct Q-3 deionized water (18.0-18.2 MQ.m resistivity). Chitosan (90% degree of deacetylation, as determined by pH titration), sodium tripolyphosphate (TPP), t-octylphenoxypolyethoxyethanol (Triton X-1000) (TX-100), glycidyltrimethylammonium chloride, and guaiazulene were purchased from Sigma-Aldrich (St. Louis, Mo.). Ultrapure sodium dodecyl sulfate (SDS) was purchased from MP Biomedicals (Solon, Ohio), and sodium chloride (NaCl) was purchased from Fisher Scientific (Fair Lawn, N.J., USA). All materials were used as received.

Synthesis of Quaternized Chitosan

The antibacterial quaternized chitosan derivative, N-[(2-hydroxy-3-trimethylammonium) propyl] chitosan chloride (HTCC), was prepared. Briefly, 2.0 g of chitosan flakes were dispersed in 38 mL of water at 85° C. and agitated with a magnetic stirrer. Three 2.45 mL aliquots of glycidyltrimetylammonium chloride were then added to the dispersion at 2 h intervals, and allowed to react for 12 h. The quaternization then became apparent from the dissolution of chitosan flakes, which are otherwise insoluble at neutral and high pH. After the reaction, the HTCC was purified by dialyzing once against 10 mM NaCl and thrice against deionized water (for 12 h each time) through a SpectralPor regenerated cellulose membrane (molecular weight cutoff=2,000). The final product was then freeze dried for 48 h on a Labconco Freeze Dryer 3 lyophilizer (Kansas City, Mo.) and characterized by $^1$H NMR to confirm that the product spectra (not shown) matched the literature spectra for HTCC.

Microgel Preparation

The quaternized chitosan microgels were prepared through the ionic cross-linking of HTCC with TPP. Briefly, 3.3 mL of 0.1 wt % TPP solution were added dropwise (at a rate of 200 RL/min) to 15 mL of 0.1 wt % HTCC solution, where each solution contained 10 mM NaCl. The addition rate was controlled with a Fisher Scientific syringe pump (Model #78-01001), and the receiving HTCC solution was stirred with a cylindrical (12 mm×4 mm) magnetic stir bar at 800 RPM inside a 20 mL scintillation vial. The microgels were then allowed to equilibrate for 15 mM, whereupon their size distributions and potentials were characterized by dynamic and electrophoretic light scattering.

Isothermal Titration Calorimetry

The binding of the anionic surfactant SDS and the nonionic surfactant TX-100 to the microgels was tested by isothermal titration calorimetry (ITC), using a Microcal VP-ITC instrument (GE Healthcare, Northampton, Mass.). In each measurement, twenty five 10-μL injections of 40 mmol/kg surfactant (either SDS or TX100) solution (containing 10 mM NaCl) were added to a 1.48 mL sample cell filled with microgel dispersions at a matching NaCl concentration. To account for the heat of surfactant dilution (and demicellization), control measurements were also performed, where 40 mM surfactant solutions were injected into microgel-free 10 mM NaCl solutions. The enthalpic signal due to binding was then obtained (as the heat absorbed from the sample cell per mole of added surfactant) by subtracting this heat of dilution from the signal obtained from the addition of surfactant to the microgels.

Dynamic and Electrophoretic Light Scattering

To determine the effect of surfactant on the size distribution and surface charge of the chitosan-based microgels, the dispersions were probed by dynamic and electrophoretic light scattering. These measurements were performed on a Zetasizer Nano ZS (Malvern, Worcestershire, UK). The effect of surfactant binding on the surface charge was inferred from the changes in $\zeta$ potential, which were estimated from the electrophoretic light scattering measurements using the Helmholtz-Smoluchowski equation. The effects of SDS and SDS:TX-100 surfactant systems on size distributions (which reflected the microgel aggregation states) was measured by dynamic light scattering (DLS), based on changes in the z-average hydrodynamic diameters (estimated via cumulant analysis). Conversely, the effects of TX-100 on microgel aggregation were characterized by analyzing the DLS data by the multiple narrow modes algorithm. This was because the microgels remained dispersed in a single phase even at high surfactant concentrations (where the scattering from the micelles became significant), and the multiple narrow modes algorithm allowed the scattering signal from the microgels to be resolved from that of the TX-100 micelles.

Colloidal Stability of Surfactant/Microgel Formulations

The short-term colloidal stability of surfactant/microgel formulations was characterized through visual observation and DLS. Concentrated surfactant and surfactant admixtures (containing either 10 mmol/kg SDS, 14.3 mmol/kg 70:30 SDS:TX-100; 25 mmol/kg 40:60 SDS:TX-100, 100 mmol/kg 10:90 SDS:TX-100, or 100 mmol/kg TX-100) were titrated into the microgel dispersions in 65- to 250 μL increments. During the titrations the surfactant/microgel formulations were continuously stirred at 800 RPM using a cylindrical (12 mm×4 mm) magnetic stir bar, and equilibrated for 6 min after each surfactant addition prior to visual analysis and DLS characterization. Each titration was performed three times and yielded reproducible results. The long-term colloidal stability was then tested by equilibrating the samples at room temperature over 6 weeks and monitoring them for precipitation.

Antibacterial Activity Tests

The effect of anionic and nonionic surfactants on the microgel antibacterial properties was probed using *Pseudomonas aeruginosa* (wild-type *P. aeruginosa* PAOI strain) as model Gram-negative bacteria. The bacteria were cultured in one-tenth strength LB broth (2.5 g/L, Difco Laboratory, Detroit, Mich.) at 37° C. until the late-exponential phase. Bacterial cells were then harvested by centrifugation at 2,000 g for 15 min (using an Eppendorf 5804R centrifuge; Hamburg, Germany), washed and resuspended in phosphate buffer (0.54 g $Na_2HPO_4$ and 0.88 g $KH_2PO_4$ per liter, pH=6.98) as bacterial suspensions ($OD_{600}$=0.25±0.02).

All glassware used in this example was sterilized in an autoclave. Likewise, the HTCC, TPP, and surfactant solutions used to prepare the surfactant/microgel formulations were sterile-filtered using Santorius Minisart NML 0.8 μm syringe filters. The microgels were filtered, and after the filtration, the microgels were prepared inside a BSL 2 certified biosafety chamber, whereupon 2 mL of surfactant (which contained either SDS, TX-100, or an admixture of both) were added at a rate of 1 mL/min, such that the final HTCC concentration was $7.4 \times 10^{-2}$ wt %. Each antimicrobial formulation sample was then tested in triplicate at room temperature (22±2° C.). The bacterial suspension was mixed with the surfactant/microgel formulations in a 1:1000 ratio (e.g., 15 μl:1:15 ml). After mixing, samples were taken at 5, 15, and 30 min to quantify the effect of surfactant/microgel formulations on the number of viable cells. The viable cells were enumerated at each time point using the heterotrophic plate count method with R2A agar plates (Difco Laboratories, Detroit, Mich.).

Dye Solubilization Tests

To test the hydrophobe solubilization properties of each surfactant/microgel formulation type, surfactant/microgels formulations were prepared as described previously using SDS:TX-100 ratios of 100:0, 70:30, 40:60, 10:90, and 0:100, and total surfactant concentrations of 1.75, 1.12, 1.04, 1.08 and 14.4 mmol/kg, respectively. The concentrations of SDS-containing samples corresponded to the maximum surfactant concentrations that were mixed with the microgels during the titrations before phase separation occurred. Conversely, the concentration of 14.4 mmol/kg was used for the 0:100 SDS:TX-100 system (in which phase separation did not occur) because it was the highest surfactant concentration tested in the colloidal stability and biocidal activity experiments. Three milliliters of each formulation type were added to a test tube and mixed with 0.2 g of hydrophobic guauazulene dye for 5 minutes on a vortex mixer. The samples were then equilibrated for 24 hours and—after separating the microgels and undissolved dye particle by passing the formulation though a Millipore Millex® FG 0.2 μm filter (to minimize artifacts due to light scattering and absorption from the microgels and undissolved dye)—quantified for the dissolved dye content by UV/Vis spectroscopy (extinction coefficient=0.2575 $mM^{-1}$ $cm^{-1}$) using a Cary 50 spectrophotometer. Each measurement was performed in triplicate.

Turbidimetric Measurements

To measure the effect of surfactant choice on formulation clarity, the turbidity of each formulation used in the dye solubilization experiment was quantified. This choice of formulation compositions, which corresponded to the maximum surfactant concentrations that were used to prepare single-phase antibacterial formulations during the surfactant titrations, reflected two considerations: (1) these surfactant concentrations optimize hydrophobe solubilization without diminishing biocidal activity; and (2) because the turbidity increases with the surfactant content, these compositions enable the measurement of maximum turbidity in the single-phase surfactant/microgel formulations obtained using each surfactant system. Here, the turbidity of dye-free surfactant/microgel formulations was measured (without filtration at $\lambda$=488 mm) immediately after the surfactant addition, using a Cary 50 spectrophotometer. Each measurement was performed three times.

Example 1

Surfactant Binding to Chitosan-Derived Microgels

The binding of anionic SDS and nonionic TX-100 to the microgels was probed by ITC and electrophoretic light scattering. When SDS was titrated into the microgel dispersion, an exothermic binding heat (of approximately 5 kJ/mol of added SDS) was detected by ITC (FIG. 1), thus showing that the SDS was binding to the microgels. Once the SDS concentration exceeded about 2 mmol/kg, however, the binding heat diminished sharply to about 0.7-0.8 kJ/mol. This transition shows the saturation of cationic binding sites. The persistence of the exothermic binding heat beyond that point, however, shows that SDS continues to bind (through non-electrostatic interactions) even after the cationic charges are saturated. Conversely, no binding heat was detected when TX-100 was added to the microgels, thus showing that TX-100 does not bind to the chitosan-derived microgels.

Figure 2:
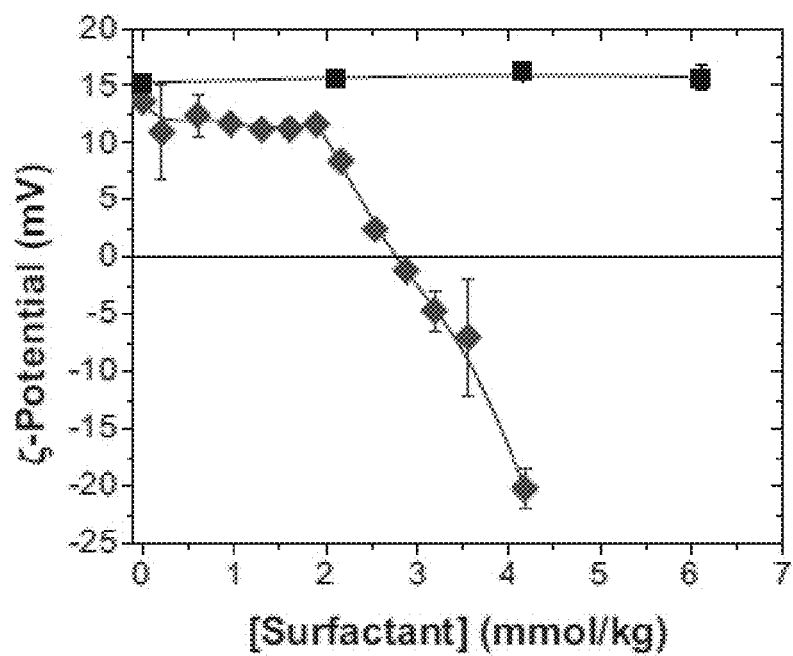
FIG. 2: Microgel ζ-potentials in the presence of (♦) SDS and (■) TX-100. (The lines are guides).

This interpretation of the molecular binding events is further supported by the ζ-potential estimates obtained by electrophoretic light scattering. Without surfactant, the microgel ζ-potential in 10 mM NaCl is about 15 mV (see FIG. 2). When SDS is added to the microgels, the ζ-potential stays nearly constant, until the SDS concentration reaches the saturation transition in the ITC data (i.e., exceeded—2 mmol/kg). At this point, the ζ-potential diminishes dramatically, and ultimately becomes negative. The microgel charge inversion that occurs after the saturation of cationic sites confirms the continued binding of SDS to the microgels, which occurs through hydrophobic association.

The addition of nonionic TX-100 (instead of the SDS) has no effect on the microgel ζ-potential. This combination of ITC and electrophoretic light scattering data shows that SDS binds to the chitosan-derived microgels and the TX-100 does not.

Example 2

Colloidal Stability of Surfactant/Microgel Formulations.

To determine the surfactant compositions at which the microgels can be dispersed, the short-term colloidal stability of the surfactant/microgel formulations was investigated by titrating concentrated surfactant solutions into dilute microgel dispersions (which initially contained $8.2 \times 10^{-2}$ wt % HTCC). Microgel aggregation was then tracked both visually and by DLS. In the absence of TX-100, the microgels—whose z-average hydrodynamic diameter was ca. 300 nm—remained dispersed until the SDS was mixed with the cationic microgels near the saturation point ([SDS]—2 mmol/kg, as shown by the ITC data and the blue diamonds in FIG. 3A). Above this point, their z-average diameters (see FIG. 3A) and polydispersities (FIG. 9) increased sharply due to coagulation, and the microgels precipitated. This coagulation reflects the neutralization of the HTCC charges on the microgel surface, which diminishes both the hydrophilicity of the microgels and the electrostatic stabilization of their dispersions.

When the SDS concentration was raised further, above 8 mmol/kg, the microgels redispersed. These transitions show the interactions of molecular HTCC and cationically-modified hydroxyethyl cellulose with anionic surfactants—i.e., where the surfactant/polyelectrolyte complexes precipitated when the surfactant and polymer were mixed at near stoichiometric ratios, and were resolubilized in the limit of high surfactant concentration. This resolubilization phenomenon is attributed to the additional binding of surfactant, which breaks up the interpolymer surfactant/polyelectrolyte aggregates, such that the polymer-bound surfactant aggregates are no longer shared by multiple polymer chains or (in the case of the present example) multiple microgels.

Figure 11:
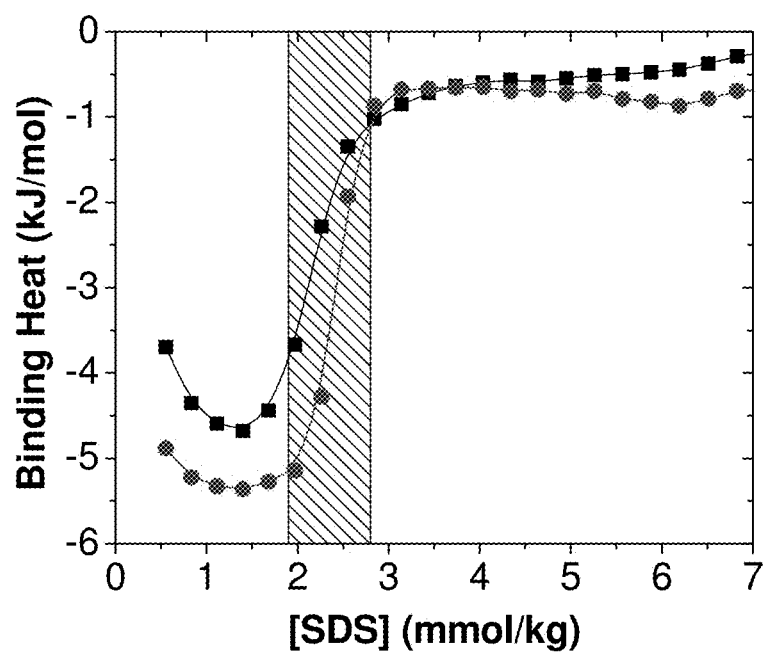
FIG. 11: ITC data for the titration of 40 mmol/kg SDS into (■) 0.082 wt % molecular N-[(2-hydroxy-3-trimethylammonium) propyl] chitosan chloride (HTCC) and (♦) HTCC/sodium tripolyphosphate (TPP) microgels (also containing 0.082 wt % HTCC) mixtures. The lines are guides to the eye, while the shaded region indicates the saturation transition.

The microgel hydrodynamic diameter diminished dramatically as the concentration was increased beyond the resolubilization boundary, and matched that obtained for SDS complexes with molecular (TPP-free) HTCC. This decrease in particle size was accompanied by a sharp reduction in dispersion turbidity, thus indicating microgel dissolution and indicating that the binding of SDS can displace ionic crosslinks formed by TPP between the HTCC chains. This is further supported by comparing the ITC data for SDS binding to HTCC/TPP microgels—where most of the binding sites were initially occupied by TPP—with its binding to molecular HTCC (without TPP), where all the binding sites were initially free. This comparison, shown in FIG. 11, reveals that the presence of TPP has little impact on the SDS concentration required to saturate the cationic HTCC binding sites. Thus, the electrostatic binding of SDS can displace the TPP crosslinks within the microgels, and can lead to their dissolution when SDS is in excess.

Figure 3A:
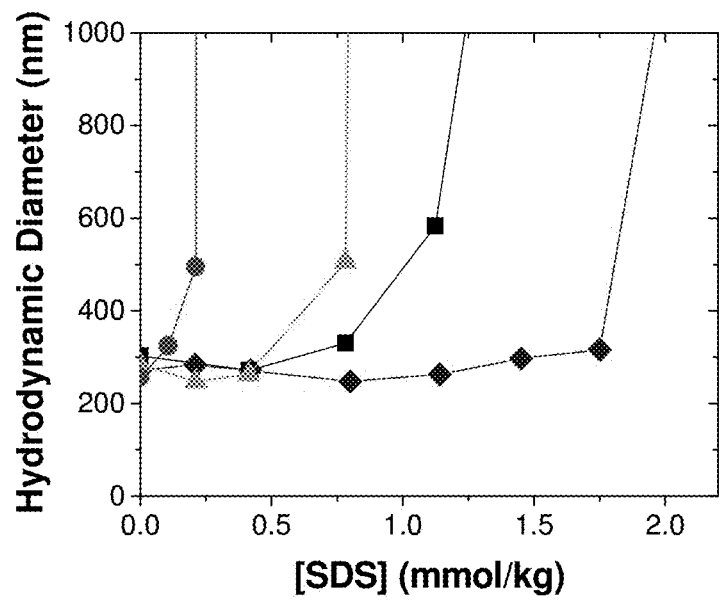
FIGS. 3A-3B: Dynamic light scattering (DLS) analysis of cationic microgel dispersions in SDS:TX-100 solutions with (♦) 100:0 (■) 70:30, (▲) 40:60 and (※) 10:90 SDS:TX-100 molar ratios, shown as function of (FIG. 3A) SDS concentration and (FIG. 3B) total surfactant concentration (with the rapid precipitation transition indicated by the shaded region). The solid lines are guides.
Figures 8, 9:
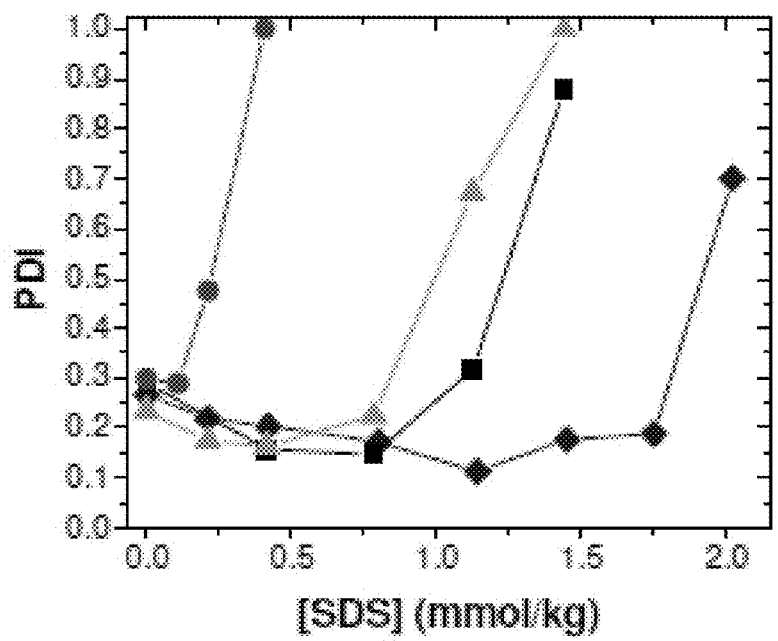
FIG. 8: Table 1. Concentrations of SDS and total surfactant at the onset of precipitation.
FIG. 9: DLS data showing the polydispersity index (PDI)-values of cationic microgel dispersions in SDS/TX-100 solutions with: (♦) 100:0 (■) 70:30, (▲) 40:60 and (※) 10:90 SDS:TX-100 molar ratios, as function of SDS concentration. The solid lines are guides to the eye.

When the surfactant titrations were repeated using tertiary SDS/TX-100/water formulations (where the SDS:TX-100 ratios were either 70:30, 40:60 or 10:90), the addition of TX-100 shifted the precipitation transition to lower SDS concentrations (see FIG. 3A and FIG. 8—Table 1).

Figure 3B:
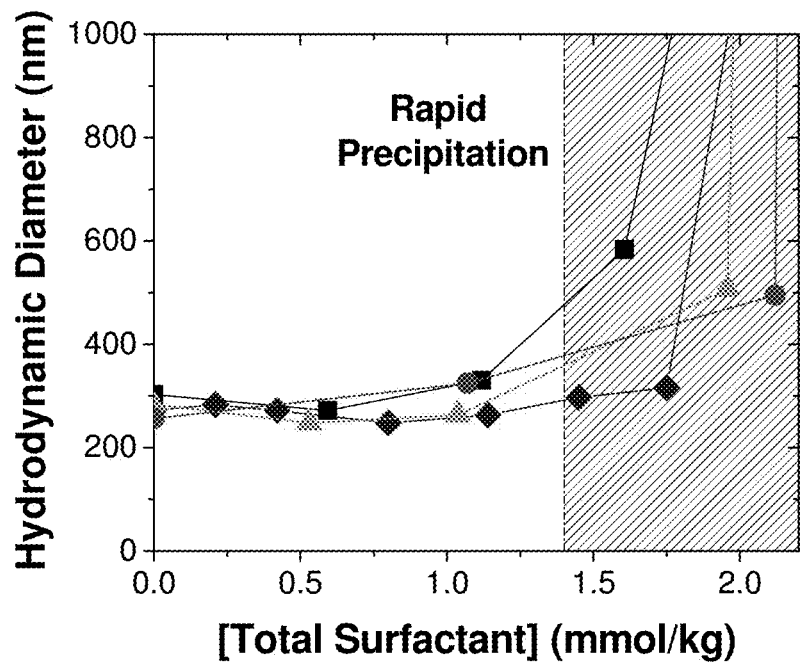
Figure 10:
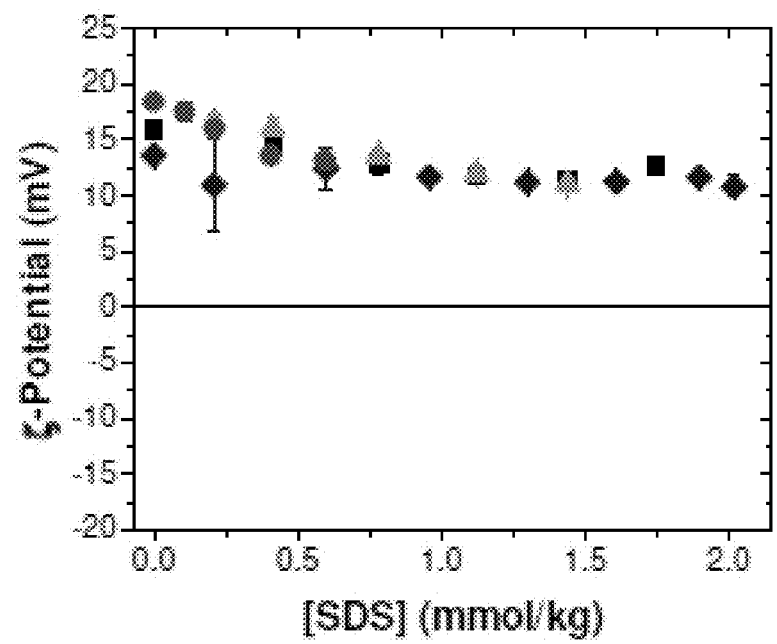
FIG. 10: The ζ-potentials of cationic microgel dispersions in SDS/TX-100 solutions with (♦) 100:0 (■) 70:30, (▲) 40:60 and (※) 10:90 SDS:TX-100 molar ratios, plotted as function of SDS concentration.

At each SDS:TX-100 ratio, precipitation occurred at roughly the same overall surfactant concentration (roughly 1.4-2 mmol/kg, as shown in FIG. 3B and FIG. 8—Table 1). This shift of the precipitation boundary to lower SDS concentrations was particularly surprising because the microgel ζ-potential in SDS/TX-100/water surfactant formulations was roughly the same as that in the absence of TX-100 at the same SDS concentration (FIG. 10). This early coagulation reflects the bridging of microgels with surface-bound SDS/TX-100 micelles (i.e., microgel/micelle heterocoagulation), even when the cationic chitosan amine groups are in excess. Unlike in the SDS/microgel formulations without TX-100, the microgels did not re-disperse in SDS/TX-100 surfactant formulations at higher concentrations (up to 100 mmol/kg).

Figure 4:
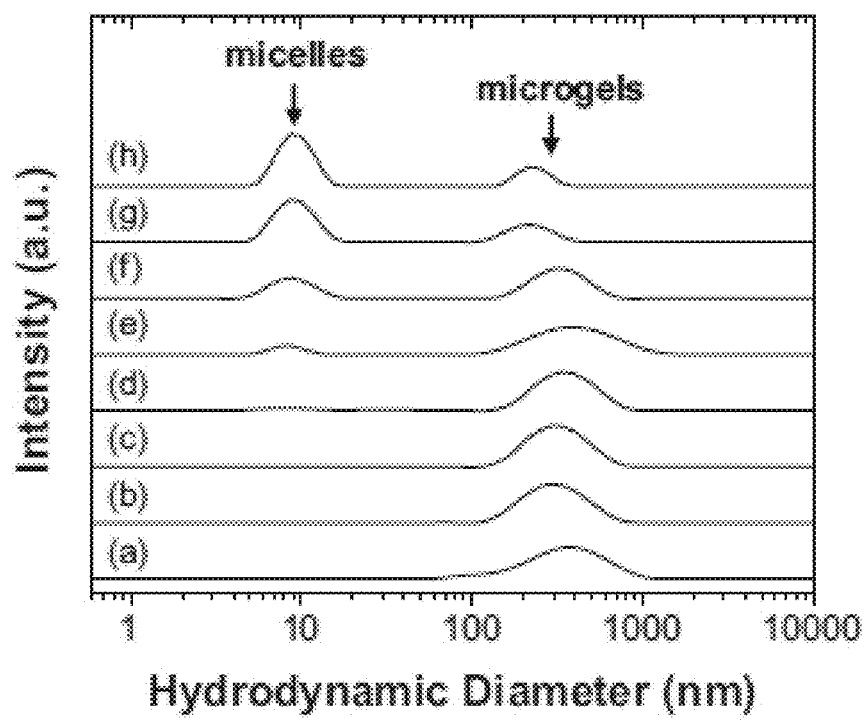
FIG. 4: DLS analysis of microgel size distributions in: (a) 0 mmol/kg, (b) 2.1 mmol/kg, (c) 4.2 mmol/kg, (d) 6.1 mmol/kg, (e) 8.0 mmol/kg, (f) 9.8 mmol/kg, (g) 11.5 mmol/kg, and (h) 14.4 mmol/kg TX-100 solutions. The curves were offset vertically for clarity.

The titration experiment was repeated using nonionic TX-100 as the only surfactant species, thereby eliminating electrostatic surfactant/microgel binding. The microgels remained dispersed at all investigated surfactant concentrations ([TX-100]≤14.4 mmol/kg) and, as shown by the DLS data in FIG. 4—where the peak at 8 nm, which grows with increasing surfactant concentration, reflects the formation of TX-100 micelles—appeared to have little impact on the microgel size distributions. This shows that surfactant-induced coagulation of cationic microgel dispersions was avoided by the use of the nonionic surfactant.

The short-term colloidal stability seen in this example reveals the restrictions on surfactant compositions that can be used with the HTCC/TPP microgels. In addition to the rapid, surfactant-induced microgel coagulation (or disintegration), however, the long-term stability of these colloidal dispersions (which is important for commercial use) can be undermined by other effects such as attractive Van der Waals interactions, bridging flocculation by surface-bound TPP, or hydrolytic degradation.

Upon storage at room temperature over longer timescales (of several days), the microgels coagulated and precipitated at nearly all SDS and SDS/TX-100 surfactant concentrations (and even without added surfactant). At low surfactant concentrations (0-2 mmol/kg), below the onset of rapid precipitation in microgel formulations with SDS and SDS/

TX-100 (see FIG. 3 and Table 1 in FIG. 8), this occurred within one or two days. This limited colloidal stability of HTCC/TPP microgels differs greatly from that of non-quaternized chitosan/TPP microgels, which remain dispersed even after several months. While not wishing to be bound by theory, it is believed that this may reflect the differences in the biopolymer/TPP binding strength, which ITC measurements suggest to be significantly weaker for HTCC than for chitosan (see FIG. 12). The microgel coagulation occurs through the ionic bridging of the microgels by TPP, which occurs more rapidly at higher free TPP concentrations. The free TPP concentration, on the other hand, scales inversely with the binding strength; thus, the faster coagulation of HTCC/TPP microgels reflects the higher concentration of bridging TPP ions in solution. This effect is also likely enhanced by the low ζ-potentials of HTCC/TPP microgels (~15 mV) which, because of the weaker electrostatic repulsion, leads to more-frequent microgel collisions.

When single-phase formulations were prepared at higher surfactant concentrations, the colloidal stability was dramatically improved. When the microgels were dispersed in 10 mmol/kg SDS (above the resolubilization phase boundary for the SDS/microgel system), the microgels remained dispersed for more than 2 weeks at room temperature. Likewise, when the microgels were mixed with 14.4 mmol/kg TX-100, the microgels remained dispersed for 5-6 weeks. This extended shelf life shows that, in addition to not causing precipitation, TX-100 dramatically enhances the long-term colloidal stability of HTCC microgel formulations. It also indicates that, despite the lack of binding signal in the ITC data (see FIG. 1), the nonionic TX-100 surfactant interacts hydrophobically with the HTCC/TPP microgels.

Example 3

Antibacterial Activity of Surfactant/Microgel Formulations

Figure 5:
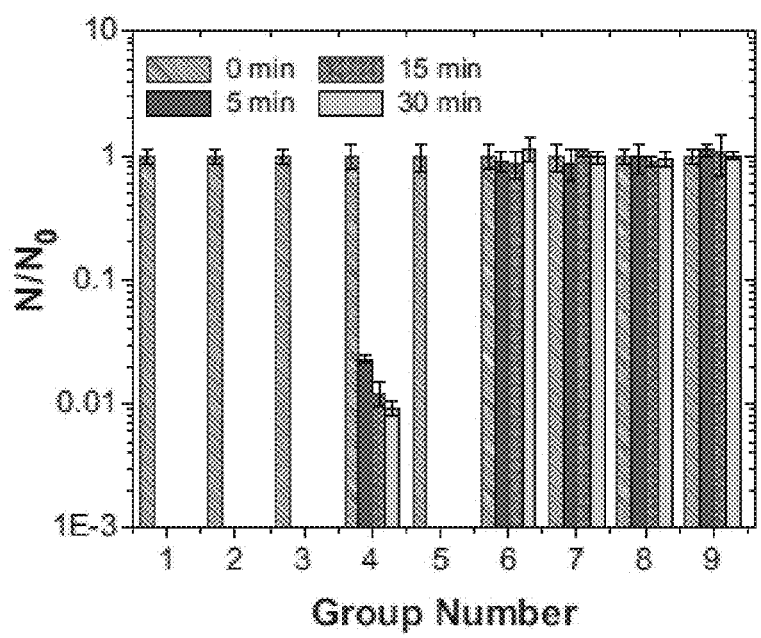
FIG. 5: Normalized *Pseudomonas aeruginosa* viable cell counts after 0-30 min of exposure to microgels mixed with: (1) water, (2) 1.0 mmol/kg SDS, (3) 3.0 mmol/kg 40:60 SDS:TX-100 mixture, (4) 10 mmol/kg SDS, and (5) 14.4 mmol/kg TX-100, and microgels-free solutions containing (6) 10 mmol/kg SDS, (7) 14.4 mmol/kg TX-100, (8) 3.0 mmol/kg 40:60 SDS:TX-100 mixture, and (9) water.

The antibacterial activity of the surfactant/microgel formulations was tested using *Pseudomonas aeruginosa* PAO1 as a model Gram-negative bacteria. As a positive control, the bacteria were added to a surfactant-free microgel dispersion (containing $7.4 \times 10^{-2}$ wt % HTCC), whereupon all bacteria were rapidly killed within the first 5 min (see FIG. 5, Group 1; where the number of viable cells, N, is normalized by their initial number, $N_o$). When SDS was added to the dispersion, such that the microgel cationic charges were not fully neutralized (i.e., 1 mmol/kg SDS; see FIG. 5, Group 2), the microgels maintained their strong antibacterial activity and again killed all the bacteria within 5 min. Similar results were obtained when the microgels were dispersed in a dilute (3 mmol/kg; see FIG. 5, Group 3) 40:60 SDS:TX-100 formulation, which had a similar SDS concentration to Group 2.

The coagulation of the microgels at this SDS:TX-100 surfactant concentration (see FIG. 3) did not appear to affect their antibacterial properties. When the SDS concentration was raised to be in excess to the HTCC amines, however (using 10 mmol/kg SDS), the antibacterial activity was diminished, with nearly 1% of the bacteria still viable after 30 min of contact time (see FIG. 5, Group 4). This reduction in antibacterial activity reflects the neutralization of the quaternary HTCC amine groups—to which the antibacterial activity is typically attributed—by the microgel-bound anionic surfactant. This neutralization is evident from the ζ-potential data in FIG. 2, where the microgel charge was shown to become negative at SDS concentrations above 2.8 mmol/kg. Furthermore, because the antibacterial activity of microgels may be stronger than that of molecular HTCC, the reduced antibacterial activity at higher SDS concentrations might also reflect microgel dissociation. Thus, the electrostatic binding of anionic surfactant to the cationic microgels diminishes both the stability and the antibacterial activity of the formulation.

Conversely, when an excess (14.4 mmol/kg) of the non-binding TX-100 was added to the microgels, the strong antibacterial properties were preserved (see FIG. 5, Group 5), and all of the bacteria were killed within 5 min of contact time. This shows that, by avoiding electrostatic binding, antibacterial activity of chitosan-based microgels can be preserved even at high surfactant concentrations.

To ensure that the surfactants used were not biocidal on their own, the cells were exposed to microgel-free SDS, TX-100 and SDS/TX-100 surfactant solutions (see FIG. 5, Groups 6-8) and water (see FIG. 5, Group 9) as negative controls. These measurements confirmed that, without the microgels, the surfactants (see FIG. 5, Groups 6-8) had no short-term effect on bacterial viability, and that the rapid antibacterial activity of the surfactant/microgel formulations stems from the microgels and not the surfactants.

Likewise, when the bacteria were exposed to water (without surfactant or microgels; see FIG. 5, Group 9), the viable cell counts remained constant over the 30 min experiment. These results show that the strong antibacterial properties of chitosan-based microgels are mediated by their cationic amine groups. Accordingly, in formulations containing nonionic and anionic surfactants, desirable antibacterial activity is achieved using either nonionic surfactants, or anionic surfactants at low concentrations (i.e., where the microgel amine groups are not neutralized).

Example 4

Hydrophobe Solubilization Properties of Surfactant/Microgel Formulations

In addition to their colloidal stability and antibacterial properties, it is desirable that successful cleaning and personal care product formulations be able to solubilize hydrophobic compounds. To this end, hydrophobe solubilization properties of microgel formulations with SDS, SDS/TX-100 and TX-100 solutions were measured. The surfactant concentrations in dispersions prepared using the SDS and SDS/TX-100 surfactant systems were selected to be near the onset of rapid precipitation (see FIG. 3B), such that the surfactant content was near the maximum that can be used without undermining the phase stability or antibacterial activity of the dispersion. Similarly, dispersions prepared using only TX-100—where no rapid precipitation or antibacterial activity reduction occurred—were prepared at the maximum TX-100 concentration used in the colloidal stability and antibacterial activity tests (i. e., 14.4 mmol/kg TX-100).

Figure 6A:
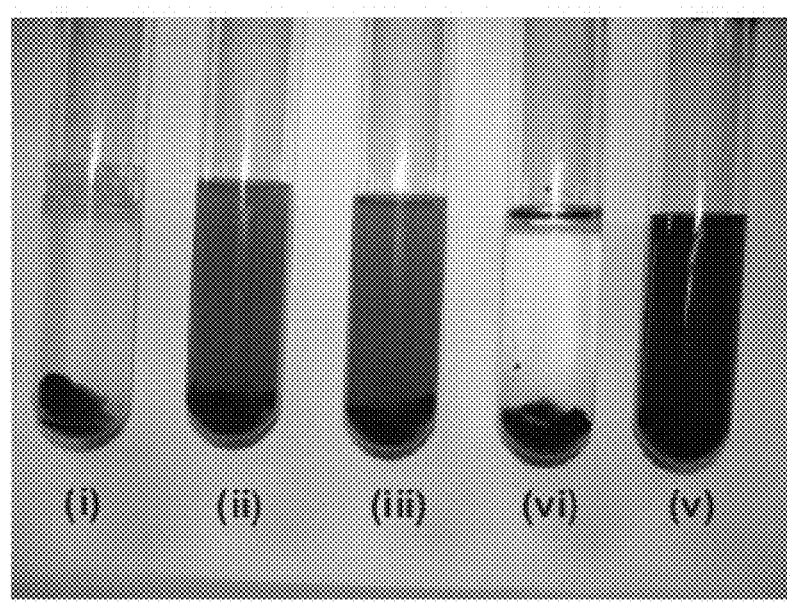
FIGS. 6A-6B: Visual observation (FIG. 6A) and spectroscopic quantification (FIG. 6B) of guaiazulene dye solubilization in surfactant/microgel dispersions containing (i) 1.75 mmol/kg SDS, (ii) 1.12 mmol/kg 70:30 SDS:TX-100, (iii) 1.04 mmol/kg 40:60 SDS:TX-100, (iv) 1.09 mmol/kg 10:90 SDS:TX-100, and (v) 14.4 mmol/kg TX-100. The spectroscopic analysis was performed after filtering out the microgels and larger dispersed dye particles from the samples.
Figure 6B:
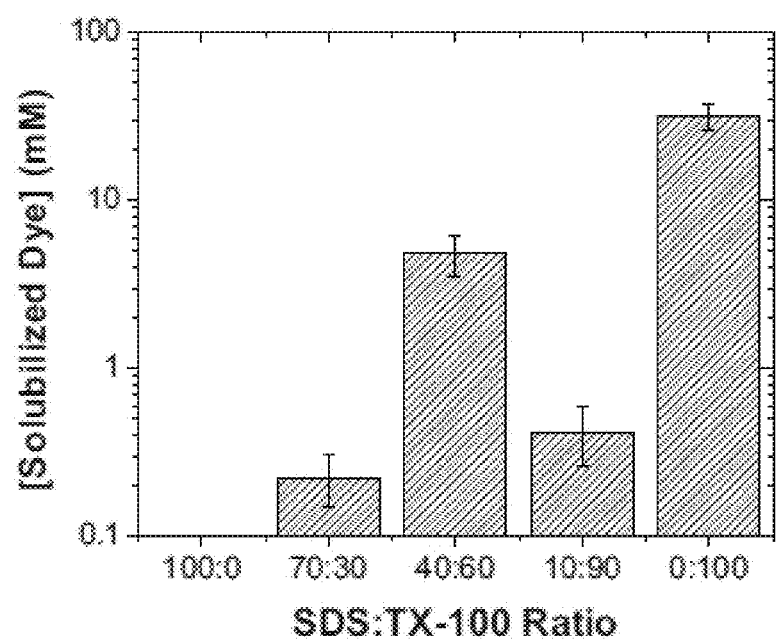

To test the hydrophobe solubilization properties of the surfactant/microgel formulations, the dispersions were mixed with hydrophobic blue (guaiazulene) dye. When the dye was mixed with the surfactant/microgel formulations, a fraction of the dye dissolved in samples containing TX-100 or SDS/TX-100 formulations. This was shown by the blue color of the surfactant/microgel formulation (see FIG. 6A, Samples ii-v), and confirmed by UV-Vis spectroscopy (FIG. 6B). No dye dissolution, however, occurred in dispersions containing SDS without TX-100 (FIG. 6A, Sample i, and FIG. 6A).

Microgel dispersions prepared using 70:30 and 40:60 SDS:TX-100 ratios also generated finely-dispersed dye particles, which were not solubilized at the molecular level. Most of these particles (along with the microgels) were removed by filtration through a 0.2 µm filter prior to spectroscopic analysis. The dye particles at the 40:60 SDS:TX-100 ratio, however, were dispersed more-finely than those at 70:30 SDS:TX-100. Consequently, the filtration of 70:30 SDS:TX-100 samples yielded clear solutions, while the filtered 40:60 SDS:TX-100 samples remained opaque. This indicated that nearly all undissolved particles were removed from the 70:30 SDS:TX-100 sample, while in the 40:60 SDS:TX-100 samples some of the dye particles remained dispersed. The presence of finely-dispersed dye particles in the 40:60 SDS:TX-100 samples made the measured solubilized dye concentration (in FIG. 6B) appear higher than it really was (and higher than it was in other SDS-bearing samples). Because of this artifact, the true dye solubility in the 40:60 SDS:TX-1001 microgel formulation is lower than it appears in the UV-Vis measurements. The microgels dispersed in 14.4 mmol/kg TX-100, however, had by far the best solubilization properties (where the solubilized dye concentration was almost seven times higher than that measured for the 40:60 SDS:TX-100 samples).

The lack of dissolved dye in dispersions containing only SDS reflected the fact that almost all of the SDS was taken up by the microgels, and was therefore unavailable to interact with the dye. The impact of SDS uptake on dye solubilization was confirmed by mixing the dye with microgel-free 1.75 mmol/kg SDS (i.e., the SDS concentration in FIG. 6A, Sample i), which yielded a dark blue mixture with finely-dispersed dye particles (see FIG. 13).

Conversely, when SDS/TX-100 formulations were used, a substantial portion of the surfactant remained outside the microgels, and enabled dye solubilization. The stable dye particle dispersions that form at 70:30 and 40:60 SDS:TX-100 ratios reflects the electrostatic repulsion that exists between dye particles coated with anionic surfactant, and shows that the surfactant/microgel formulations are able to remove hydrophobic soils without molecular solubilization. However, because the SDS-free microgel/TX-100 formulation can be prepared at higher surfactant concentrations (without compromising colloidal stability or antibacterial activity), the nonionic surfactant-based formulations (e.g., FIG. 6A, Sample v) provide the best solubilization properties.

Example 5

Effects of Surfactant on Mixture Turbidity

Besides being functional, it is desirable that consumer product formulations be aesthetically appealing. For products sold in clear packaging, clarity is a key optical property.

Figure 7A:
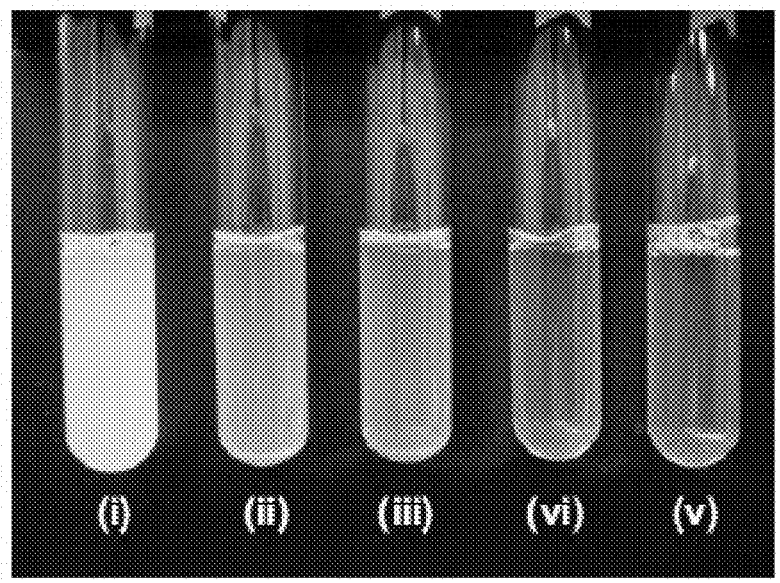
FIGS. 7A-7B: Photographs (FIG. 7A) and turbidimetry measurements (FIG. 7B) showing the effects of surfactant at (i) 100:0, (ii) 70:30, (iii) 40:60, (iv) 10:90 and (v) 0:100 SDS:TX-100 ratios on the clarity of surfactant/microgel dispersions.
Figure 7B:
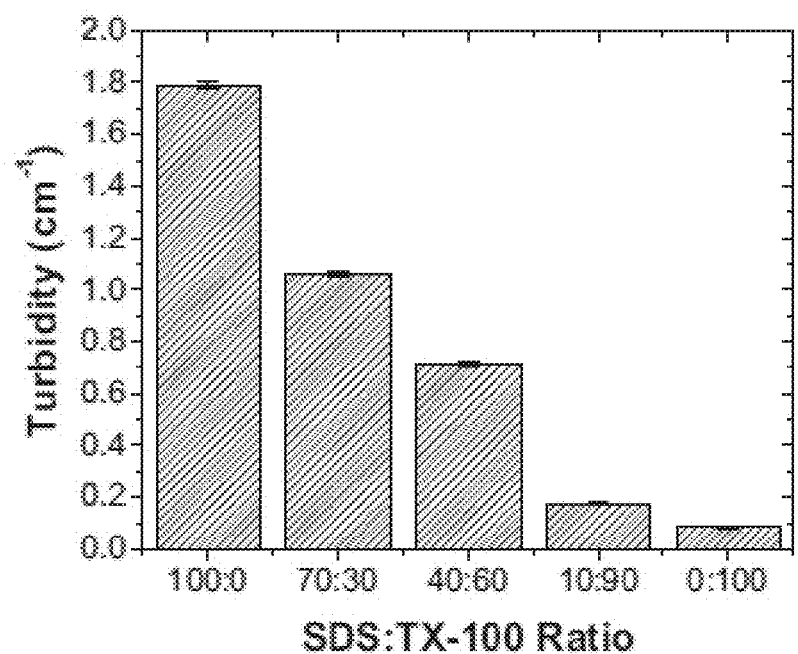

The effect of surfactant on the turbidity of the chitosan-based microgel dispersions was characterized at the same surfactant concentrations as were used in the hydrophobe solubilization tests (see FIG. 7).

The dispersion clarity depended strongly on the SDS content. When only SDS was added to the microgels (without TX-100), the turbidity increased dramatically, despite the nearly-constant hydrodynamic diameter of the microgels (see FIG. 3). This reflects a greater refractive index contrast between the microgel and solvent phases, which stems from the uptake of organic SDS molecules into the aqueous microgel particles.

When SDS/TX-100 surfactant formulations were used, the turbidity increase became progressively less-pronounced with decreasing SDS:TX-100 ratios, showing a smaller extent of surfactant uptake by the microgels. Likewise, when SDS-free TX-100 was used, the turbidity remained virtually unchanged by the addition of surfactant. This result shows that the clarity of the nonionic surfactant/microgel formulations is not diminished by the uptake of surfactants into the microgels (like it is in the case of anionic surfactants), and that microgel dispersions with nonionic surfactants exhibit superior optical properties to their ionic surfactant-containing counterparts.

Thus, these examples show that the chitosan-derived microgels are highly antibacterial, and are useful alternatives to cationic surfactants and other low-molecular-weight antibacterial agents. In addition, the mixing of chitosan-derived microgels with a nonionic surfactant (TX-100) preserves the chitosan-derived microgel's antibacterial activity and low optical density, does not lead to rapid, surfactant-induced precipitation (which limits the range of surfactant concentrations that can be used), and enhances long-term colloidal stability.

Furthermore, because the addition of nonionic surfactant does not undermine the biocidal activity and colloidal stability of the microgels, the nonionic surfactant/microgel formulations can be prepared at high surfactant concentrations, which provide superior hydrophobe solubilization.

Conversely, chitosan-based microgel formulations with anionic (SDS) and anionic/nonionic (SDS/TX-100) surfactant formulations undergo rapid, surfactant-induced precipitation. In the case of mixed anionic/nonionic surfactant systems this limits the single-phase formulation compositions to very low surfactant concentrations, which lead to poor hydrophobe solubilization properties.

When microgels are mixed with only anionic surfactant, however, the formulations remain in a single phase both in the limits of low and high surfactant concentrations (with surfactant-induced precipitation occurring at intermediate concentrations). As in the case of the anionic/nonionic surfactant formulations, formulations at low anionic surfactant concentration exhibit poor hydrophobe solubilization properties (which are worse than those in anionic/nonionic surfactant formulations).

Conversely, at higher anionic surfactant concentrations (above the CMC, where single-phase mixtures again form), the binding of surfactant to the microgels weakens their biocidal activity and ultimately leads to microgel dissolution. Furthermore, the uptake of anionic surfactant by the microgels makes the microgels more opaque, thereby potentially making the anionic surfactant/microgel formulations less-suitable for clear packaging.

Also, HTCC/TPP microgels mixed with anionic surfactant (or without surfactant) exhibit poor long-term colloidal stability, and coagulate within days. These results show that stable formulations that combine antibacterial activity with good solubilization and optical properties, surfactant/chitosan-based microgel formulations are achieved when nonionic surfactant systems are used in the formulations.

Example 6

Evolution in Microgel Polydispersity

FIG. 9 shows the evolution in the microgel polydispersity index (PDI) during the titration of surfactant (either SDS or SDS/TX-100 at 70:30, 40:60 and 10:90 SDS:TX-100 ratios). At low surfactant concentrations, the addition of surfactant gradually diminishes the PDI. At the onset of precipitation, however (where the microgels begin to rapidly coalesce), the PDI-values increase sharply. The sharp increase in PDI-values reflects the formation of polydisperse microgel flocs.

Example 7

Evolution in ζ-Potential

FIG. 10 shows the evolution in the microgel ζ-potential during the titration of surfactant (either SDS or SDS/TX-100 in 70:30, 40:60 and 10:90 SDS:TX-100 ratios), plotted as a function of SDS concentration. The overlap between the data points collected at different SDS:TX-100 ratios reveals that (despite the effect of TX-100 on microgel coagulation) the microgel ζ-potential is unaffected by TX-100.

Example 8

Critical Micelle Concentrations of SDS/TX-100 Formulations

To confirm that coagulation in SDS/TX-100/microgel formulations occurred at surfactant concentrations above the surfactant critical micelle concentration (CMC), the CMCs of SDS/TX-100 formulations in 10 mM NaCl were measured by isothermal titration calorimetry (ITC). The results of these measurements are presented in FIG. 11, which shows that the microgels coagulate (and precipitate) at surfactant concentrations above the CMC.

Example 9

ITC Analysis of TPP Binding to HTCC

Figure 12:
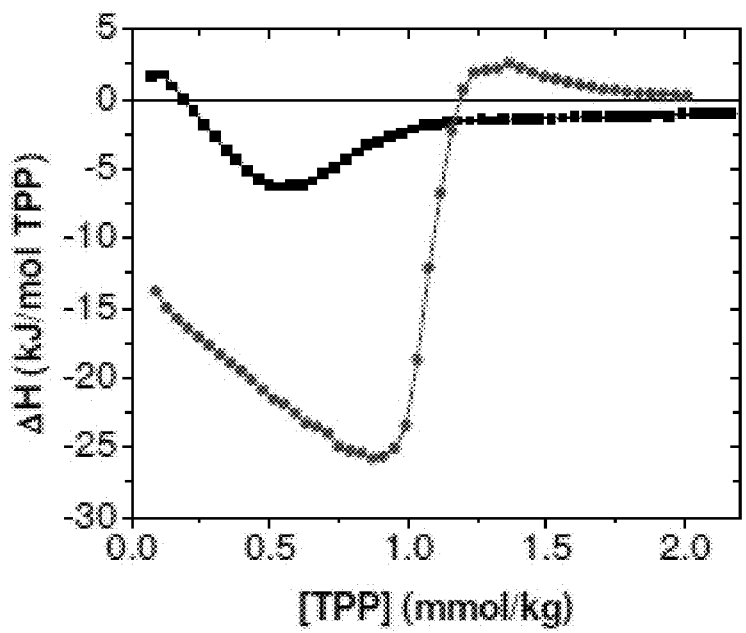
FIG. 12: ITC data for the titration of 0.4 wt % TPP into (■) 0.1 wt % HTCC and (※) 0.1 wt % chitosan solutions. The lines are guides to the eye.

The strength of chitosan/ionic crosslinker binding can be shown from isothermal titration calorimetry (ITC) data. FIG. 12 compares the ITC data for TPP binding to chitosan (red circles) and HTCC (which was used to prepare the microgels; black squares). The data in these plots are roughly proportional to the first derivative of the binding isotherm when plotted as a function of total binding ligand (in this case TPP) concentration. Consequently, the abruptness of the saturation transition (where the exothermic binding signal diminishes to approximately 0 kJ/mol) reflects the binding strength of each polymer/crosslinker system. Comparing these transitions for the two data sets—where the saturation transition for the chitosan/TPP system is much more abrupt than that for the HTCC/TPP system—shows that the binding of TPP to HTCC is much weaker than its binding to chitosan.

Example 10

Dye Solubilization in Microgel-Free SD

Figure 13:
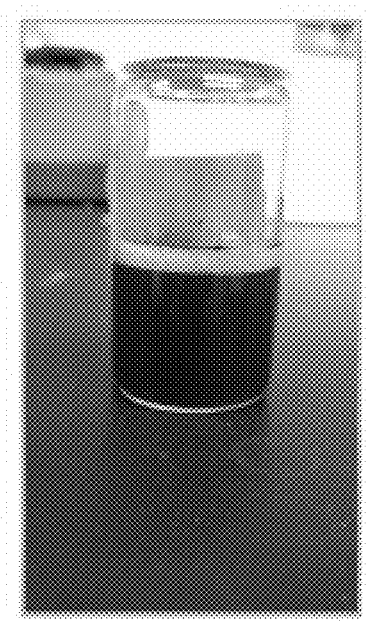
FIG. 13: A photograph of guaiazulene blue dye mixed with 1.75 mmol/kg SDS solution.

FIG. 13 shows a photograph of hydrophobic (guaiazulene) blue dye equilibrated for 24 h with 1.75 mmol/kg SDS solution. The uniform blue color in this formulation is in stark contrast with the clear supernatant that forms in 1.75 mmol/kg SDS solution (FIG. 6A, Sample i), and shows that the inability of this SDS/microgel formulation to solubilize the dye stems from the uptake of surfactant into the microgel.

Example 11

Exemplary Uses

Non-limiting uses include medical, dental, personal care and industrial uses. Non-limiting specific examples include: textiles, food and beverages; biopharmaceuticals, medical implants, wound dressings, dentistry implants and implements, packaging materials, article, compound, composition, film, yarn, fabric, mesh, screen material and the like. Other uses include use as cleaning agents, antibacterial agents, antiseptic agents, and the like.

It is to be understood that the formulations described herein may be the form of a tablet, powder, gel, capsule, liquid, coating, film, foam, sponge, woven material, non-woven material, knitted material, textiles, papers, porous material or solid material.

Also, within the contemplated scope of the invention herein are article comprising a porous or solid material at least partially coated with the formulation; and/or at least partially comprised of the formulation.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. An antimicrobial formulation comprising:
   a nonionic surfactant providing colloidal stability to the formulation, wherein the nonionic surfactant comprises a hydrophilic polyethylene oxide chain and is selected from the group consisting of a polyoxypropylene glycol alkyl ether, a glycol octylphenol ether, an ethoxylated alkylphenol, a glucoside alkyl ether, and a polyoxyethylene glycol alkylphenol ether; and
   a quaternized polymeric chitosan microgel dispersed in a solution of the nonionic surfactant;
   wherein the quaternized polymeric chitosan microgel comprises particles having a size distribution in the range of about 10 nm to about 1000 nm; and
   wherein the antimicrobial formulation is essentially free of cationic surfactants.

2. The antimicrobial formulation of claim 1, wherein the quaternized polymeric chitosan microgel comprises at least one quaternized chitosan selected from the group consisting of N-[(2-hydroxy-3-trimethylammonium) propyl] chitosan chloride; hydroxypropyl chitosan; N,N,N-trimethyl chitosan; N,N,N-dimethyl chitosan propyl-(QuatPropyl); N,N,N-dimethyl chitosan butyl-(QuatButyl); N,N,N-dimethyl chitosan hexyl (QuatHexyl); N-(4-N,N-dimethylaminocinnamyl) chitosan chloride; N,N-octylchitosan; N-benzylchitosan; N-(4-methylbenzylchitosan); N-(4-hydroxybenzyl) chitosan; N-(2-methoxybenzyl) chitosan; N-(4-methoxybenzyl) chitosan; N-(3,4-dimethoxybenzyl) chitosan; N-(4-fluorobenzyl) chitosan; N-(4-chlorobenzyl) chitosan; N-(3-bromobenzyl) chitosan; N-(4-bromobenzyl) chitosan; N-(4-trifluorobenzyl) chitosan; N-(4-nitrobenzyl) chitosan; N-(4-carboxybenzyl) chitosan; N-(4-pyridinylmethyl) chitosan; N-(2-thiophenylmethyl) chitosan; and combinations thereof.

3. The antimicrobial formulation of claim 1, wherein the total concentration of the quaternized polymeric chitosan microgel ranges from about 0.01% to about 0.5%, by weight.

4. The antimicrobial formulation of claim 1, wherein the total concentration of the quaternized polymeric chitosan microgel is about 0.1%, by weight.

5. The antimicrobial formulation of claim 1, wherein the nonionic surfactant is present at a concentration, based on the total weight of the formulation, of about 250 mmol/kg or less, about 100 mmol/kg or less, about 25 mmol/kg or less, about 15 mmol/kg or less, or about 5 mmol/kg or less.

6. The antimicrobial formulation of claim 1, wherein the quaternized polymeric chitosan microgel comprises N-[(2-hydroxy-3-trimethylammonium) propyl] chitosan chloride.

7. The antimicrobial formulation of claim 6, wherein the nonionic surfactant is present at a concentration ranging from about 0.05% to about 1%, by weight per volume of the formulation in water; and the N-[(2-hydroxy-3-trimethylammonium) propyl] chitosan chloride is present at a concentration ranging from about 0.01% to about 3%, by weight per volume of the formulation in water.

8. The antimicrobial formulation of claim 1, wherein the quaternized polymeric chitosan microgel is prepared by ionic cross-linking of quaternized chitosan with sodium tripolyphosphate.

9. The antimicrobial formulation of claim 1, further comprising at least one aqueous carrier material.

10. The antimicrobial formulation of claim 1, further comprising an anionic surfactant present at a concentration such that amine groups on the quaternized polymeric microgel are not neutralized.

11. The antimicrobial formulation of claim 10, wherein the anionic and nonionic surfactants are present in a concentration ratio of from about 30:70 to about 40:60, respectively.

12. The antimicrobial formulation of claim 11, wherein the anionic and nonionic surfactants are present in a surfactant admixture and have a concentration ratio of about 40:60, respectively, the quaternized polymeric microgel is dispersed in the surfactant admixture, and the surfactant admixture has a concentration of about 3 mmol/kg or less, based on the weight of the formulation.

13. The antimicrobial formulation of claim 10, wherein the anionic surfactant is present at a concentration, based on the total weight of the formulation, of about 2 mmol/kg or less, about 1 mmol/kg or less, or about 0.5 mmol/kg or less.

14. The antimicrobial formulation of claim 10, wherein the anionic surfactant comprises one or more alkali metal $C_{8-18}$ alkyl sulfates.

15. The antimicrobial formulation of claim 14, wherein the alkali metal $C_{8-18}$ alkyl sulfates are selected from the group consisting of sodium lauryl sulfate, sodium laureth sulfates, alkyl ether sulfates, alkyl benzene sulfonates, fatty acids, and fatty acid salts.

16. The antimicrobial formulation of claim 15, wherein the anionic surfactant is sodium dodecyl sulfate.

17. The antimicrobial formulation of claim 1, wherein the antimicrobial formulation is in the form of a tablet, powder, gel, capsule, liquid, coating, film, foam, sponge, woven material, non-woven material, knitted material, textile material, porous material, or solid material.

18. An article comprising a porous or solid material comprising, or at least partially coated with, the antimicrobial formulation of claim 1.

19. An antimicrobial formulation comprising:
a nonionic surfactant present at a concentration in the range of from about 0.05% to about 3%, by weight of the formulation, wherein the nonionic surfactant comprises a hydrophilic polyethylene oxide chain and is selected from the group consisting of a polyoxypropylene glycol alkyl ether, a glycol octylphenol ether, an ethoxylated alkylphenol, a glucoside alkyl ether, and a polyoxyethylene glycol alkylphenol ether; and,
a quaternized polymeric chitosan microgel dispersed in a solution of the nonionic surfactant and present at a concentration ranging from about 0.01% to about 0.15%, by weight of the formulation.

20. The antimicrobial formulation of claim 19, wherein the quaternized polymeric chitosan microgel comprises N-[(2-hydroxy-3-trimethylammonium) propyl] chitosan chloride.

* * * * *